US012692429B2

(12) United States Patent
Somerville et al.

(10) Patent No.: US 12,692,429 B2
(45) Date of Patent: Jul. 28, 2026

(54) LIGNIN-BASED COMPOSITIONS AND RELATED HYDROCARBON SEPARATION METHODS

(71) Applicant: LignoSol IP Limited, San Gwann (MT)

(72) Inventors: Desmond Alexander Somerville, San Gwann (MT); Patrick Dieter Waibel, San Gwann (MT)

(73) Assignee: LignoSol IP Limited, San Gwann (MT)

( * ) Notice: Subject to any disclaimer, the term of this patent is extended or adjusted under 35 U.S.C. 154(b) by 95 days.

(21) Appl. No.: 18/285,422

(22) PCT Filed: Apr. 5, 2022

(86) PCT No.: PCT/IB2022/053145
§ 371 (c)(1),
(2) Date: Oct. 3, 2023

(87) PCT Pub. No.: WO2022/214950
PCT Pub. Date: Oct. 13, 2022

(65) Prior Publication Data
US 2024/0182776 A1 Jun. 6, 2024

(30) Foreign Application Priority Data

Apr. 6, 2021 (GB) ...................................... 2104865
Nov. 8, 2021 (GB) ...................................... 2115987

(51) Int. Cl.
| | |
|---|---|
| C09K 8/582 | (2006.01) |
| C09K 8/584 | (2006.01) |
| C09K 8/592 | (2006.01) |
| C12N 1/205 | (2026.01) |
| C12R 1/07 | (2006.01) |

(52) U.S. Cl.
CPC .............. *C09K 8/582* (2013.01); *C09K 8/584* (2013.01); *C09K 8/592* (2013.01); *C12N 1/205* (2021.05); C09K 2208/18 (2013.01); *C12R 2001/07* (2021.05)

(58) Field of Classification Search
CPC ........ C09K 8/582; C09K 8/584; C09K 8/592; C09K 2208/18; C12N 1/205; C12B 2001/07
See application file for complete search history.

(56) References Cited

U.S. PATENT DOCUMENTS

| | | | |
|---|---|---|---|
| 3,438,895 A | 4/1969 | Edmonsond et al. | |
| 3,864,276 A | 2/1975 | Benko et al. | |
| 4,101,394 A | 7/1978 | Johnson | |
| 4,133,385 A | 1/1979 | Kalfoglou | |
| 4,304,572 A | 12/1981 | Wiese et al. | |
| 4,392,941 A | 7/1983 | Roth et al. | |
| 4,793,826 A * | 12/1988 | Hayes ..................... | C10L 1/326 |
| | | | 516/70 |

| | | |
|---|---|---|
| 4,877,517 A | 10/1989 | Bulatovic et al. |
| 5,028,238 A | 7/1991 | von Rybinski et al. |
| 5,059,332 A | 10/1991 | Satoh |
| 5,114,597 A | 5/1992 | Rayborn et al. |
| 5,164,480 A | 11/1992 | Huibers et al. |
| 5,246,602 A | 9/1993 | Forrest |
| 5,248,329 A | 9/1993 | Rusin et al. |
| 5,316,664 A | 5/1994 | Gregoli et al. |
| 5,316,682 A | 5/1994 | Keyser et al. |
| 5,344,625 A | 9/1994 | Clough |
| 5,368,972 A | 11/1994 | Yamashita et al. |
| 5,711,383 A | 1/1998 | Terry et al. |
| 5,743,945 A | 4/1998 | Yamashita et al. |
| 5,911,276 A | 6/1999 | Kieke |
| 6,306,800 B1 | 10/2001 | Samuel et al. |
| 6,348,436 B1 | 2/2002 | Langlois et al. |
| 8,450,260 B2 | 5/2013 | Crawford et al. |
| 8,455,226 B2 | 6/2013 | De Windt et al. |
| 8,741,256 B1 | 6/2014 | Harrison |
| 8,748,153 B2 | 6/2014 | Tadic et al. |
| 10,362,786 B2 | 7/2019 | Chen et al. |
| 10,829,833 B2 | 11/2020 | Gos et al. |
| 12,275,894 B2 | 4/2025 | Somerville et al. |
| 2002/0044887 A1 | 4/2002 | Jones |
| 2006/0177661 A1 | 8/2006 | Smith et al. |
| 2007/0045198 A1 | 3/2007 | Sugiura |

(Continued)

FOREIGN PATENT DOCUMENTS

| | | |
|---|---|---|
| CA | 1132452 A | 9/1982 |
| CA | 2425424 A1 | 4/2002 |

(Continued)

OTHER PUBLICATIONS

International Search Report (ISR) and Written Opinion for International Application No. PCT/IB22/59176, mailed Jan. 26, 2023 (9 pages).
Nazari et al., "Study relationships between flotation variables and recovery of coarse particles in the absence and presence of nanobubble," Colloids and Surfaces A: Physicochemical and Engineering Aspects 559:284-8 (Sep. 27, 2018).
Search and Examination Report for Application No. GB2116007.2, dated Nov. 25, 2021 (8 pages).
Written Opinion for International Application No. PCT/IB22/59176, mailed Jan. 26, 2023 (6 pages).
Beisl et al., "Lignin from Micro- to Nanosize: Production Methods." Int. Journal of Molecular Sciences. 18(6): 1244 (Jun. 10, 2017) (31 pages).

(Continued)

*Primary Examiner* — Silvana C Runyan
(74) *Attorney, Agent, or Firm* — Clark & Elbing LLP

(57) ABSTRACT

Compositions are provided for hydrocarbon separation applications. In some embodiments, the composition comprises lignin, in particular technical lignin, and at least one strain of bacteria capable of biosurfactant production and/or a biosurfactant produced by at least one such isolated strain of bacteria. Also provided is a method for separating hydrocarbons from a hydrocarbon-containing material.

8 Claims, 7 Drawing Sheets

(56) References Cited

U.S. PATENT DOCUMENTS

| | | | |
|---|---|---|---|
| 2009/0011972 A1 | 1/2009 | Suzuki et al. | |
| 2009/0082227 A1* | 3/2009 | Hnatow | C02F 3/344 |
| | | | 507/201 |
| 2009/0211960 A1 | 8/2009 | Nilsen et al. | |
| 2009/0266541 A1 | 10/2009 | Reynolds et al. | |
| 2009/0291861 A1 | 11/2009 | Sawdon | |
| 2009/0308612 A1 | 12/2009 | Weaver et al. | |
| 2010/0137168 A1 | 6/2010 | Quintero et al. | |
| 2010/0233050 A1 | 9/2010 | Gargulak et al. | |
| 2011/0277991 A1* | 11/2011 | Toledo | E21B 43/006 |
| | | | 435/243 |
| 2012/0247763 A1 | 10/2012 | Rakitsky et al. | |
| 2013/0274150 A1 | 10/2013 | Holt et al. | |
| 2014/0261077 A1 | 9/2014 | Merck et al. | |
| 2014/0371071 A1 | 12/2014 | Nitsche | |
| 2015/0166836 A1 | 6/2015 | Liu et al. | |
| 2015/0285051 A1 | 10/2015 | Miller et al. | |
| 2016/0168272 A1 | 6/2016 | Retsina et al. | |
| 2016/0236158 A1 | 8/2016 | Bauer | |
| 2017/0029691 A1 | 2/2017 | Faust, Jr. et al. | |
| 2017/0306264 A1 | 10/2017 | Peggau et al. | |
| 2018/0148632 A1 | 5/2018 | Bennett et al. | |
| 2018/0265794 A1 | 9/2018 | Dahlstrand et al. | |
| 2018/0355446 A1 | 12/2018 | Medoff et al. | |
| 2019/0031945 A1 | 1/2019 | Guo et al. | |
| 2019/0055459 A1 | 2/2019 | Zelenev et al. | |
| 2019/0093463 A1 | 3/2019 | Hardin et al. | |
| 2019/0184350 A1 | 6/2019 | Terasaka et al. | |
| 2019/0382649 A1 | 12/2019 | Jiang et al. | |
| 2019/0390405 A1 | 12/2019 | Geigle et al. | |
| 2020/0032128 A1 | 1/2020 | Farmer et al. | |
| 2020/0157408 A1 | 5/2020 | Farmer et al. | |
| 2020/0172788 A1 | 6/2020 | Farmer et al. | |
| 2020/0255466 A1 | 8/2020 | Lintinen et al. | |
| 2020/0352016 A1 | 11/2020 | Bohdy | |
| 2021/0261451 A1 | 8/2021 | Patton | |
| 2021/0261459 A1 | 8/2021 | Alibek et al. | |

FOREIGN PATENT DOCUMENTS

| | | | | |
|---|---|---|---|---|
| CA | 2535702 A1 | 3/2005 | | |
| CA | 2547100 A1 | 11/2006 | | |
| CA | 2640005 A1 | 8/2007 | | |
| CA | 2661202 C | 11/2011 | | |
| CA | 2723591 C | 7/2013 | | |
| CA | 2705147 C | 9/2014 | | |
| CA | 2921996 A1 | 3/2015 | | |
| CA | 2693008 C | 4/2016 | | |
| CA | 2988826 A1 | 12/2016 | | |
| CA | 2791256 C | 6/2017 | | |
| CA | 3048404 A1 | 7/2018 | | |
| CA | 3052048 A1 * | 8/2018 | | C10G 32/00 |
| CA | 3052465 A1 | 8/2018 | | |
| CA | 3054686 A1 | 9/2018 | | |
| CA | 3058761 A1 | 10/2018 | | |
| CA | 2999599 C | 12/2019 | | |
| CA | 2772395 C | 1/2020 | | |
| CA | 2720739 C | 4/2020 | | |
| CA | 2950089 C | 4/2020 | | |
| CA | 2831902 C | 5/2020 | | |
| CA | 2877367 C | 12/2020 | | |
| CA | 2945194 C | 7/2022 | | |
| CA | 2886934 C | 1/2023 | | |
| CN | 85105225 A | 7/1986 | | |
| CN | 101104177 A | 1/2008 | | |
| CN | 104152129 A | 11/2014 | | |
| CN | 104321422 A | 1/2015 | | |
| CN | 103636599 B | 3/2015 | | |
| CN | 205527917 U | 8/2016 | | |
| CN | 106188857 A | 12/2016 | | |
| CN | 108441223 A | 8/2018 | | |
| CN | 106217826 B | 9/2018 | | |
| CN | 108623112 A | 10/2018 | | |
| CN | 109943299 A | 6/2019 | | |

| | | | |
|---|---|---|---|
| CN | 110616062 A | 12/2019 | |
| GB | 2514202 A | 11/2014 | |
| GB | 2605591 A | 10/2022 | |
| JP | 2011-121002 A | 6/2011 | |
| JP | 2017029892 A | 2/2017 | |
| KR | 101711607 B1 | 3/2017 | |
| KR | 10-2018-0130070 A | 12/2018 | |
| RU | 2188935 C1 | 9/2002 | |
| WO | WO-1992/19349 A1 | 11/1992 | |
| WO | WO-2005/028592 A1 | 3/2005 | |
| WO | WO-2012/151524 A2 | 11/2012 | |
| WO | WO-2013/037643 A1 | 3/2013 | |
| WO | WO-2015/065981 A1 | 5/2015 | |
| WO | WO-2016/053345 A1 | 4/2016 | |
| WO | WO-2016/196680 A1 | 12/2016 | |
| WO | WO-2018/064689 A1 | 4/2018 | |
| WO | WO-2019/067356 A1 | 4/2019 | |
| WO | WO-2019/112970 A1 | 6/2019 | |
| WO | WO-2019/191296 A1 | 10/2019 | |
| WO | WO-2019/213055 A1 | 11/2019 | |
| WO | WO-2020/028253 A1 | 2/2020 | |
| WO | WO-2020/060529 A1 | 3/2020 | |
| WO | WO-2020/072735 A1 | 4/2020 | |
| WO | WO-2020/149756 A2 | 7/2020 | |
| WO | WO-2020/264073 A1 | 12/2020 | |
| WO | WO-2021/015633 A1 | 1/2021 | |
| WO | WO-2021/052939 A1 | 3/2021 | |

OTHER PUBLICATIONS

Bicca et al., "Production of Biosurfactant By Hydrocarbon Degrading Rhodococcus Ruber and Rhodococcus Erythropolis." Revista de Microbiologia. 30: 231-236 (1999) (6 pages).

Chang et al., "A novel nano-lignin-based amphoteric copolymer as fluid-loss reducer in water-based drilling fluids." Colloids and Surfaces A. 583:123979 (Sep. 21, 2019) (10 pages).

Hruzová et al., "Organosolv lignin hydrophobic micro- and nanoparticles as a low-carbon footprint biodegradable flotation collector in mineral flotation." Bioresource Technology. 306:123235 (Mar. 23, 2020) (4 pages).

International Search Report and Written Opinion for International Application No. PCT/IB22/53145 mailed Jun. 27, 2022 (9 pages).

International Search Report and Written Opinion for International Application No. PCT/IB22/53147 mailed Jun. 15, 2022 (9 pages).

International Search Report and Written Opinion for International Application No. PCT/IB22/53148 mailed Jun. 27, 2022 (9 pages).

International Search Report and Written Opinion for International Application No. PCT/IB22/53151 mailed Jun. 29, 2022 (9 pages).

International Search Report and Written Opinion for International Application No. PCT/IB22/53158 mailed Jun. 21, 2022 (8 pages).

International Search Report and Written Opinion for International Application No. PCT/IB22/53160 mailed Jun. 29, 2022 (7 pages).

International Search Report and Written Opinion for International Application No. PCT/IB22/53161 mailed Jun. 27, 2022 (6 pages).

International Search Report and Written Opinion for International Application No. PCT/IB22/53162 mailed Jul. 1, 2022 (7 pages).

Li, Qingxin, "Rhamnolipid synthesis and production with diverse resources." Front. Chem. Sci. Eng. 11(1): 27-36 (Mar. 22, 2017) (10 pages).

Negi et al., "A review on lignin utilization in petroleum exploration, petroleum products formulation, bio-fuel production, and oil spill clean-up." Biomass Conversion and Biorefinery. 13: 1417-1428 (Nov. 5, 2020) (12 pages).

Sauki et al., "Extracted Lignin from Rhizophora's Black Liquor as Fluid Loss Control Additive in Water Based Drilling Mud." Key Engineering Materials. 755: 74-80 (Aug. 20, 2018) (8 pages).

Schneider et al., "Assessment of Morphological, Physical, Thermal, and Thermal Conductivity Properties of Polypropylene/ Lignosulfonate Blends." Materials. 14(3): 543 (Jan. 23, 2021) (10 pages).

Search and Examination Report for Application No. GB2104859.0, dated May 11, 2021 (8 pages).

Search and Examination Report for Application No. GB2104860.8, dated May 4, 2021 (8 pages).

Search and Examination Report for Application No. GB2104862.4, dated May 21, 2021 (8 pages).

(56) References Cited

OTHER PUBLICATIONS

Search and Examination Report for Application No. GB2104865.7, dated Jun. 8, 2021 (8 pages).

Search and Examination Report for Application No. GB2104869.9, dated Apr. 16, 2021 (6 pages).

Search and Examination Report for Application No. GB2104870.7, dated Jun. 2, 2021 (7 pages).

Search and Examination Report for Application No. GB2104877.2, dated May 10, 2021 (6 pages).

Search and Examination Report for Application No. GB2104883.0, dated May 4, 2021 (8 pages).

Search and Examination Report for Application No. GB2115987.6, dated Dec. 15, 2021 (6 pages).

Solihat et al., "Lignin as an Active Biomaterial: A Review." Jurnal Sylva Lestari. 9(1): 1-22 (Jan. 2021) (22 pages).

EP Application No. EP4320192, Extended European Search Report (EESR), Search Opinion, and Supplementary Search Report, dated Jan. 17, 2025 (11 pages).

GB Application No. GB2214123.8, Search and Examination Report, dated Nov. 18, 2022 (8 pages).

Madhu, "Difference Between Anolyte and Catholyte", published Online Sep. 19, 2020, at: https://www.differencebetween.com/difference-between-anolyte-and-catholyte/, (3 pages).

PCT Application No. PCT/IB23/59500, International Search Report (ISR) and Written Opinion, mailed Feb. 2, 2024 (8 pages).

Schneider et al., "Assessment of Morphological, Physical, Thermal, and Thermal Conductivity Properties of Polypropylene/Lignosulfonate Blends", Materials, (Jan. 2021) vol. 14; 543 (10 pages).

This vs. That: Anolyte vs. Catholyte, published Online at: https://thisvsthat.io/anolyte-vs-catholyte, (2023) (2 pages).

* cited by examiner

R          X          X          X          X          X

R          R          R          X          R          X          R          X          R          X

LIGNIN-BASED COMPOSITIONS AND RELATED HYDROCARBON SEPARATION METHODS

CROSS-REFERENCE TO RELATED APPLICATIONS

This application claims priority to GB Provisional Patent Application No. 2104865.7, filed 6 Apr. 2021, and GB Provisional Patent Application No. 2115987.6, filed 8 Nov. 2021, the disclosures of which are hereby incorporated by reference in their entireties.

BACKGROUND OF THE INVENTION

This invention relates to the separation of hydrocarbons from hydrocarbon-containing materials. More particularly, the present invention relates to lignin-based hydrocarbon separation compositions for hydrocarbon separation applications and related methods.

A myriad of techniques exist for the separation and recovery of hydrocarbons from various hydrocarbon-containing materials, be they particulate hydrocarbon containing materials or liquid hydrocarbon-containing materials, or the like. In the oil and gas industry, the hydrocarbon containing materials include oil sands, as well as natural gas and oil from subterranean reservoirs.

Oil sands, also referred to as tar sands, are a type of unconventional petroleum deposit found in countries such as Canada, Venezuela, Kazahkstan, and Russia. These deposits are typically a complex mixture of particulate matter such as sand, quartz crystal or clay, with heavy oil, extra heavy oil and/or bitumen, and water.

Various techniques exist for extracting oil from oil sands, such as cold heavy oil production with sand (CHOPS), cyclic steam stimulation (CSS), steam assisted gravity drainage (SAGD), vapour extraction (VAPEX), toe to heel air injection (THAI), combustion overhead gravity drainage (COGD), or a combination of these techniques. Some oil sands deposits that are located close to the surface may also be extracted using surface mining techniques, typically followed by a hot or warm water separation process. Each of these techniques have at least one disadvantage, including using large quantities of water, using large amounts of energy, and/or requiring the use of chemicals that are environmentally harmful and/or costly.

Moreover, hydrocarbon contamination of ground material and/or water due to oil and gas extraction processes, or pipeline leaks, is a significant environmental problem. For example, hot water extraction of surface-mined oil sands produces large volumes of oil sands tailings, which typically comprise a mixture of water, sand, quartz crystal, clay, and residual bitumen. Pipeline leaks may produce mixtures of oil and soil or sand, often also with water. Similarly, oil spills at sea may produce mixtures of oil and water. Separation of the hydrocarbons from the ground material and/or water may be difficult and expensive.

For instance, the use of analogue ionic liquids for the separation of hydrocarbons from particulate matter has been proposed in U.S. Pat. No. 9,447,329. However, the reagents used are costly and may make the process economically infeasible.

SUMMARY OF THE INVENTION

In one aspect of the invention, there is provided a method for separating hydrocarbons from a hydrocarbon-containing material, the method comprising:

providing a composition comprising lignin and at least one isolated strain of bacteria capable of producing at least one biosurfactant, and/or at least one biosurfactant produced from at least one bacteria capable of producing a biosurfactant, the composition having a solids content of about 50% or above, in particular of about 50% to about 60%; and contacting the hydrocarbon-containing material with the composition, thereby to separate out at least a portion of the hydrocarbons from the hydrocarbon-containing material.

In some embodiments, the hydrocarbon-containing material comprises hydrocarbon-containing particulate matter.

In some embodiments, contacting the hydrocarbon-containing material with the composition comprises mixing the particulate matter with the composition to form a mixture.

In some embodiments, the hydrocarbon-containing material comprises a hydrocarbon-containing liquid.

In some embodiments, contacting the hydrocarbon-containing material with the composition comprises flowing the hydrocarbon-containing liquid through the composition.

In another aspect of the invention, there is provided a hydrocarbon separation composition suitable for separating hydrocarbons from a hydrocarbon-containing material, the composition comprising lignin, in particular technical lignin, and at least one isolated strain of bacteria capable of producing at least one biosurfactant, and/or at least one biosurfactant produced from at least one isolated strain of bacteria capable of producing a biosurfactant, the composition having a solids content of about 50% or above, in particular of about 50% to about 60%.

In some embodiments, the hydrocarbon separation composition further comprises a catholyte solution.

In some embodiments, the catholyte solution is a stabilized or upgraded catholyte solution.

The invention extends to the use of lignin, in particular technical lignin, in the separation of hydrocarbons from a hydrocarbon-containing material.

Other aspects and features of the present invention will become apparent, to those ordinarily skilled in the art, upon review of the following description of specific embodiments of the disclosure.

BRIEF DESCRIPTION OF THE DRAWINGS

The invention will now be described in more detail, by way of example only, with reference to the accompanying drawings in which.

DESCRIPTION OF PREFERRED EMBODIMENTS

Figure 1:
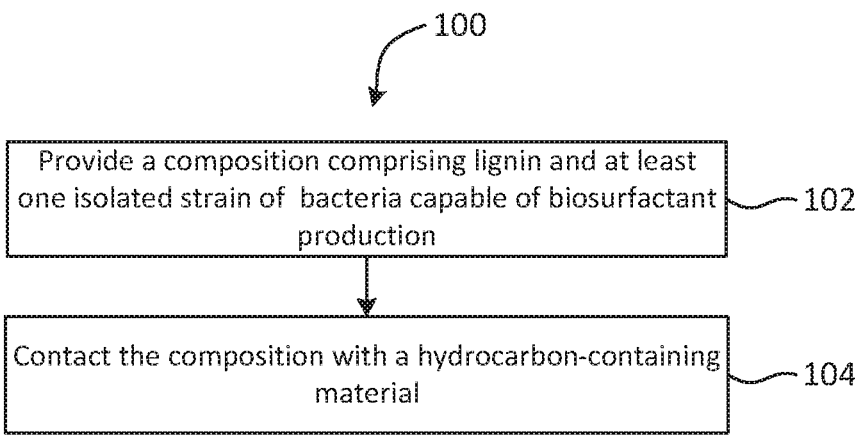
FIG. 1 is a flowchart of an example method for separating hydrocarbons from a hydrocarbon-containing material, according to some embodiments.

The hydrocarbon separation compositions of the invention, in particular lignin-based hydrocarbon separation compositions, are provided for hydrocarbon separation applications and related methods.

In some embodiments, the hydrocarbon-containing material comprises hydrocarbon-containing particulate matter. As used herein, "particulate matter" refers to matter comprising solid particles. In some embodiments, the hydrocarbon-containing particulate matter is relatively free of water. In other embodiments, the hydrocarbon-containing particulate matter may comprise at least a portion of water.

The particulate matter may comprise solid particles of materials found in the ground, including but not limited to: sand, clay, soil, silt, rock, solid mineral or metal particles, and the like. In other embodiments, the particulate matter may comprise solid particles associated with processing of hydrocarbons, such as metal particles from drilling or process equipment.

In some embodiments, the hydrocarbon-containing material may comprise particulate matter extracted from a subterranean reservoir. As used herein, "reservoir" refers to any subterranean region, in an earth formation, that includes at least one pool or deposit of hydrocarbons therein.

In some embodiments, the reservoir is an oil sands reservoir. Oil sands, also known as tar sands and bituminous sands, are naturally occurring deposits of viscous oil in loose sands or partially consolidated sandstone. As used herein, "viscous oil" refers to hydrocarbon material having high viscosity and high specific gravity. In some embodiments, viscous oil comprises heavy oil and/or bitumen. Heavy oil may be defined as a hydrocarbon material having a viscosity greater than 100 centipoise (0.1 Pa/s) under reservoir conditions and an API gravity of 20° API or lower. Bitumen may be defined as a hydrocarbon material having a viscosity greater than 10,000 centipoise (10 Pa/s) under reservoir conditions and an API gravity of 10° API or lower.

In some embodiments, the oil sands ore may be extracted by a surface mining process. The term "surface mining" in this context refers to extraction of oil sands ore from an open pit or burrow. Surface mining is used for viscous oil deposits located relatively close to the surface. For example, surface mining operations at the Athabasca oil sands in Alberta, Canada typically involve excavating oil sands ore from a mine pit using hydraulic or electric shovels. The ore is then further processed, including, for example, crushing the ore into smaller particles and mixing the ore with hot or warm water (optionally with caustic soda) to form a slurry that can be conveyed for further processing. Raw or processed oil sands ore or oil sands slurry may be used in the methods described herein.

In other embodiments, the particulate matter may comprise soil or other ground material contaminated with at least one hydrocarbon. For example, the particulate matter may comprise soil and/or sand contaminated due to a pipeline leak of crude oil or processed oil in the form of gasoline, or the like. As another example, the particulate matter may comprise soil and/or sand contaminated with natural gas.

In other embodiments, the hydrocarbon-containing material may comprise a hydrocarbon-containing fluid. In some embodiments, the hydrocarbon-containing fluid comprises a multiphase fluid. As used herein, "multiphase fluid" refers to a fluid comprising more than one phase such as a liquid, solid and/or gas phase. In other embodiments, the hydrocarbon-containing fluid may comprise a hydrocarbon-containing liquid that is relatively free of solid material and/or gas.

In some embodiments, the hydrocarbon-containing fluid may comprise an emulsion. For example, the fluid may comprise an oil-water emulsion such as an oil-in-water emulsion or a water-in-oil emulsion. In some embodiments, the emulsion may further comprise at least a portion of particulate matter. As one example, water-in-oil emulsions may be produced during crude oil recovery due to naturally occurring water in the reservoir. Such emulsions may also comprise at least a portion of entrained sand, clay, or the like.

In some embodiments, the hydrocarbon-containing fluid comprises tailings from an oil recovery operation. Conventional oil sands mining operations separate the bitumen from the sand and clay of the oil sands ore using hot or warm water extraction, which produce large volumes of wastewater (i.e. tailings). The tailings are typically stored in large man-made tailings ponds. Tailings from oil sands surface mining operations may comprise a mixture of residual viscous oil (bitumen), salts, suspended solids, and dissolved salts, organics, and minerals.

In other embodiments, the hydrocarbon-containing fluid may comprise drill cuttings from drilling of oil or gas wells. The drill cuttings may comprise solid particulate matter removed from the borehole and brought to the surface in the drilling fluid. The drilling fluid (also called "drilling mud") may comprise water, a water-based mud (WBM), an oil-based mud (OBM), a synthetic-based mud (SBM) or any other suitable type of mud.

In other embodiments, the hydrocarbon-containing fluid may comprise a liquid contaminated with one or more hydrocarbons. For example, the hydrocarbon-containing liquid may comprise fresh water or seawater contaminated by a crude oil spill, mixtures of oil and water resulting from rinsing of oil tankers or storage facilities, for example.

In other embodiments, the hydrocarbon-containing material may comprise any other suitable material and embodiments are not limited to the specific materials described herein.

As used herein, "lignin" refers to a biopolymer that is found in the secondary cell wall of plants and some algae. Lignin is a complex cross-linked phenolic polymer with high heterogeneity. Typical sources for the lignin include, but are not limited to, softwood, hardwood, and herbaceous plants such as corn stover, bagasse, grass, and straw, for example.

In some embodiments, the lignin comprises technical lignin. As used herein, "technical lignin" refers to lignin that has been isolated from lignocellulosic biomass, for example, as a byproduct of a pulp and paper production or a lignocellulosic biorefinery. Technical lignins may have a modified structure compared to native lignin and may contain impurities depending on the extraction process. In some embodiments, the technical lignin comprises at least one of Kraft lignin, lignosulfonates, soda lignin, organosolv lignin, steam-explosion lignin, and enzymatic hydrolysis lignin. In other embodiments, the technical lignin may comprise any other form of technical lignin.

In embodiments where the lignin comprises lignosulfonates, the lignosulfonates may be in the form of a salt including, for example, sodium lignosulfonate, calcium lignosulfonate, or ammonium lignosulfonate.

In other embodiments, the technical lignin is in the form of unhydrolyzed Kraft black liquor. Black liquor is a byproduct of the Kraft process and may contain not only lignin but hemicellulose, inorganic chemicals used in the pulping process, and other impurities. In other embodiments, the technical lignin is in the form of "brown liquor" (also referred to as red liquor, thick liquor or sulfite liquor), which refers to the spent liquor of the sulfite process. In other embodiments, the technical lignin may be in the form of any other spent cooking liquor of a pulping process or any other suitable lignin-based byproduct.

In other embodiments, the lignin may be synthetic lignin or any other suitable type of lignin.

In some embodiments, the lignin is hydrolyzed. As used herein, "hydrolyze" refers to using acid or base hydrolysis at least partially to separate lignin from the polysaccharide content of the lignocellulosic biomass. For example, where the lignin is in the form of black liquor, carbon dioxide may be used to precipitate Kraft lignin from the black liquor and then the Kraft lignin may be neutralized with sodium hydroxide.

In some embodiments, the lignin is in an aqueous suspension. As used herein, an "aqueous suspension" of lignin refers to solid particles of lignin suspended, dispersed, and/or dissolved in a solvent that at least partially comprises water. In some embodiments, the solvent comprises substantially all water. In other embodiments, the solvent may comprise a combination of water and any other suitable solvent.

In some embodiments, the aqueous suspension of lignin may have a solids content of about 10% to about 90%, or about 25% to about 75%, or about 30% to about 60%, or about 33% to about 55%. In some embodiments, the aqueous suspension of lignin may have a solids content of about 50% to about 60%. In some embodiments, the aqueous suspension of lignin may have a solids content of about 10% or above, or of about 25% or above, or of about 30% or above, or of about 33% or above or of about 50% or above. In some embodiments, the aqueous suspension of lignin may have a solids content of about 90% or below, or of about 75% or below, or of about 60% or below, or of about 55% or below. In some embodiments, the aqueous suspension has a solids content of about 46%. A solids content of about 33% to about 55% may allow the composition to be flowable, which may be preferred for some applications. In other applications, the composition may be used as a slurry and the solids content may be as high as about 85% to about 90%.

In some embodiments, the lignin comprises at least one of lignin nanoparticles and lignin microparticles. As used herein, "nanoparticle" refers to a particle in the nanometer size range, for example, between about 1 nm and about 100 nm, and "microparticle" refers to a particle in the micrometer size range, for example, between about 100 nm and about 1000 µm (1 mm). In some preferred embodiments, the lignin particles have a size of about 200 nm or less, or about 100 nm or less. In some preferred embodiments, at least about 20%, or at least 30%, or at least 40%, or at least 50%, or at least 60%, or at least 70%, or at least 80%, or at least 90% of the lignin particles are nanoparticles having a size of about 100 nm or less.

The lignin nanoparticles and/or microparticles can be produced by any suitable method. For example, the lignin nanoparticles and/or microparticles can be produced using at least one of: solvent shifting; pH shifting; cross-linking polymerization; mechanical treatment; ice-segregation; template-based synthesis; aerosol processing; electro spinning; and carbon dioxide ($CO_2$) antisolvent treatment. Such methods are described in Beisl et al. "Lignin from Micro- to Nanosize: Production Methods" *Int. J. Mol. Sci.* 2017; 18: 1244, incorporated herein by reference in its entirety.

In some preferred embodiments, lignin nanoparticles are produced using a pH shifting method, for example, as disclosed in Beisl et al. Briefly, the starting lignin material may be dissolved in a basic solution (e.g. an aqueous NaOH solution at pH 12) and the pH of the solution may be gradually decreased by addition of acid (e.g. $HNO_3$) to precipitate lignin nanoparticles. The solution may then be neutralized (e.g. by addition of NaOH) to re-suspend the nanoparticles. The resulting particles may have a size of about 200 nm or less, or about 100 nm or less. In other embodiments, the lignin nanoparticles may be produced by any other suitable method.

By providing the lignin in the form of lignin nanoparticles and/or microparticles, the surface area of the lignin is increased, thereby also increasing the negative force around each particle. In addition, lignin nanoparticles and/or microparticles may have improved solubility in water. Conventional lignins are typically only soluble in water at alkaline pH; however, nanoparticles and/or microparticles may be soluble in approximately neutral water (Beisl et al.), which may be preferred for some applications.

In some embodiments, where the lignin comprises an aqueous suspension of lignin nanoparticles, the zeta potential value of the suspension may be about −5 to about −80 mV. In some embodiments, the specific gravity of the aqueous suspension of lignin nanoparticles is between about 1.286 to about 1.7 SG.

The composition further comprises at least one isolated strain of bacteria capable of biosurfactant production and/or at least one biosurfactant produced from at least one isolated strain of bacteria capable of producing a biosurfactant.

As used herein, "isolated" or "isolate", when used in reference to a strain of bacteria, refers to bacteria that have been separated from their natural environment. In some embodiments, the isolated strain or isolate is a biologically pure culture of a specific strain of bacteria. As used herein, "biologically pure" refers to a culture that is substantially free of other organisms.

As used herein, "biosurfactant" refers to compounds that are produced at the bacterial cell surface and/or secreted from the bacterial cell and function to reduce surface tension and/or interfacial tension. Non-limiting examples of biosurfactants include lipopeptides, surfactin, glycolipids, rhamnolipids, methyl rhamnolipids, and viscosin, for example. The isolated strain may be capable of producing one or more types of biosurfactant.

In some embodiments, the isolated strain may produce one or more additional active compounds. For example, the isolated strain may produce a biopolymer, solvent, acid, exopolysaccharide, and the like.

In some embodiments, the at least one isolated strain of bacteria comprises a strain of *Bacillus*. In other embodiments, the at least one isolated strain comprises a strain of bacteria capable of biosurfactant production and that is non-pathogenic. Non-limiting examples of suitable strains are listed in Satpute et al. "Methods for investigating biosurfactants and bioemulsifers: a review" *Critical Reviews in Biotechnology*, 2010, 1-18. For example, the at least one isolated strain of *Bacillus* may be *Bacillus* amyloliquefaciens, *Bacillus licheniformis, Bacillus pumilus, Bacillus subtilis*, or combinations thereof, and in particular *Bacillus licheniformis*.

In some embodiments, the pH of the composition may be selected or adjusted to provide a suitable pH for the isolated strain(s). In some embodiments, the composition may further comprise one or more nutrients to support growth of the bacteria such as, for example, acetate, one or more vitamins, and the like.

In some embodiments, the isolated strain is in a viable form. For example, in some embodiments, the isolated strain may be in the form of a liquid suspension. In some embodiments, the isolated strain may be incubated for a suitable period of time prior to incorporation into the composition such that at least a portion of biosurfactant(s) is/are secreted into the bacterial suspension and therefore can be incorporated into the composition. For example, the bacteria can be incubated/fermented for between about one day and about six months or longer. The isolated strain may be incubated in the presence of a nutrient source and under suitable conditions (e.g. temperature, agitation, etc.) to produce the biosurfactant(s).

In other embodiments, the isolated strain may be in a lyophilized (freeze-dried) form. In some embodiments, the freeze-dried form comprises freeze-dried spores.

In some embodiments, where the isolated strain is in the form of a liquid suspension or in a freeze-dried form, the composition may comprise approximately 40 billion CFU (colony forming units) and may be combined with at least about 1 g of lignin and up to several tons of lignin.

In other embodiments, the isolated strain may be in an inviable form. For example, the isolated strain may be in the form of heat-killed cells or a cell lysate. In these embodiments, the bacteria of the isolated strain may be incubated for a suitable period of time prior to loss of viability (e.g. heat killing or lysis) such that a sufficient quantity of biosurfactant(s) is/are secreted into the bacterial suspension for incorporation into the composition. For example, the bacteria may be incubated for at least one week prior to loss of viability.

In other embodiments, a liquid suspension of bacteria may be incubated to produce the biosurfactant(s) and a supernatant containing the biosurfactant(s) may be separated from the bacterial cells and used in the composition.

Without being limited by theory, it is believed that the combination of lignin and the biosurfactant produced by the isolated strain act to mimic the natural habitat of the biosurfactant producing strains. The lignin may function as a growth substrate that contains required nutrients (carbon and fructose) to support growth of the bacteria, with the exception of additional acetate and metallic vitamins, which may be added to the composition as needed.

In addition, a series of drop collapse tests were conducted to evaluate additional benefits of combining the lignin with a suitable biosurfactant in the composition of the invention. In particular, the tests were carried out to determine the effectiveness of the compositions of the invention in reducing the surface tension of water and other liquids. The results indicated that a further advantage in combining the lignin and biosurfactant in the composition of the invention is a significant reduction in surface tension at concentrations of between about 10 ppm and 300 ppm of the biosurfactant, which assists significantly in the compositions ability to cut through hydrocarbon containing materials.

In some embodiments, the lignin-based separation compositions of the invention further comprise catholyte solutions. As used herein, "catholyte solution" is an activated solution produced in an electrochemical reaction, and is that part of the electrolyte solution adjacent the cathode of an electrochemical cell. It can be produced, for instance, from a 0.05%-1% salt brine (NaCl or KCl), and has a pH in the range 10.0 to 13.0 and an ORP/Redox value of less than about −800 mV, typically in the order of −900 to −950 mV. In the case of an NaCl starting solution, the active ingredient is highly active, and typically unstable, NaOH.

The separation compositions of the invention can comprise from about 1% to about 75% by volume of the catholyte solution.

In some embodiments, the composition further comprises at least one of a carboxylic acid or a salt or ester thereof. In some embodiments, the carboxylic acid is a di-carboxylic acid or a salt or ester thereof. The carboxylic acid or salt/ester thereof may function as a solvent, for example, by facilitating formation of a stable emulsion of the various components of the composition. In some embodiments, the composition comprises a carboxylic acid ester. In some embodiments, the carboxylic acid ester comprises a methyl ester or a butyl ester. In some embodiments, the butyl esters are produced by biochemical metathesis. In some embodiments, the butyl ester comprises n-Butyl 4-oxopentanoate. In some embodiments, the methyl ester comprises unsaturated $C_{10}$ or $C_{12}$ methyl ester. In some embodiments, the methyl ester comprises methyl 9-decenoate or methyl 9-dodecenoate. In some embodiments, the methyl ester is produced from a plant oil feedstock.

In some embodiments, the composition further comprises carbon black. The carbon black may be electroconductive carbon black and the carbon black may function to increase the conductivity of the composition. In some embodiments, the carbon black may be conductive, superconductive, extra-conductive or ultraconductive carbon black. In some embodiments, the carbon black may be in the form of carbon black beads, microparticles, and/or nanoparticles. For example, the carbon black may comprise Printex™ XE2 B Beads from Orion Engineered Carbons™. In some embodiments, the composition may comprise about 0.5% to about 10% carbon black by volume. In some embodiments, addition of carbon black may increase the negative zeta potential of the composition thereby increasing its electrical stability. In other embodiments, the composition may comprise any other highly conductive microparticle and/or nanoparticle.

In some embodiments, the composition may comprise about 1% to about 30%, or about 1% to about 20%, or about 1% to 10% of di-carboxylic acid and/or butyl esters by volume.

In some embodiments, the composition is gasified with a gas. As used herein, "gasified" refers to introduction of a gas into the composition such that bubbles of the gas are suspended therein. The term "aerated" refers to gasifying with air or oxygen. The gas may be selected based on the aerobic or anaerobic nature of the isolated strain(s) incorporated into the composition. In some embodiments, the gas at least partially comprises oxygen. For example, the gas may be air or relatively pure oxygen. In some embodiments, the gas may at least partially comprise carbon dioxide and/or nitrogen. Gasification may function to provide oxygen and/or or other suitable gasses directly or in close proximity to the bacterial cells of the isolated strain. Gasification may promote proliferation of the bacterial cells and allow the composition to be used or stored for an extended period of time. In some embodiments, the aerated composition may have a half-life of about 20 to 30 days.

In some embodiments, the composition is gasified with nanobubbles and/or microbubbles of the gas. As used herein, "nanobubble" refers to bubbles in the nanometer range and "microbubble" refers to bubbles in the micrometer range. The nanobubbles and/or microbubbles may be introduced into the composition by any suitable means including, for example, a micro- or nanobubble nozzle or a venturi tube.

It has surprisingly been found that using a stabilized or upgraded as opposed to an otherwise unstable catholyte solution enhances the action of the compositions of the invention. Accordingly, in some embodiments, the catholyte solution is pre-treated in a system that is designed to introduce nitrogen gas into the catholyte solution, in particular in the form of nano- and/or micro-bubbles, for incorporation into a composition of the invention.

Accordingly, in some embodiments, the catholyte solution is upgraded prior to blending with the other components of the separation composition.

The compositions disclosed herein may be useful for various separation applications in the recovery and/or processing of hydrocarbons including, for example, hydrocarbon separation, demulsification of oil-in-water emulsions, and separation from particulate matter. Embodiments of the compositions may be used in ambient temperatures (for example, between about 2° C. and about 25° C.) and function via a rotational barrier repulsion mechanism.

In some embodiments, the composition may comprise any other suitable components. For example, in some embodiments, the composition may further comprise at least one nutrient source for the live bacteria of the isolated strain.

Therefore, in some embodiments, a relatively non-toxic, inert, and sustainable composition is provided for hydrocarbon separation. The composition may also be relatively low cost as lignin is a waste product of pulp and paper operations that is typically discarded.

FIG. 1 is a flowchart of an example method 100 for separating at least a portion of hydrocarbons from a hydrocarbon-containing material, according to some embodiments.

At block 102, a composition is provided comprising lignin and at least one isolated strain of bacteria capable of biosurfactant production. The composition may be any embodiment of the composition described above. The term "provided" in this context may refer to making, receiving, buying, or otherwise obtaining the composition.

At block 104, the hydrocarbon-containing material is contacted with the composition. The term "contact" in this context may refer to any means by which the composition may be brought into contact with the hydrocarbon-containing material. In some embodiments, the composition may be introduced into the hydrocarbon-containing material. In other embodiments, the hydrocarbon-containing material may be introduced into the composition. In some embodiments, the composition and hydrocarbon-containing material may be combined, for example, by mixing, blending, homogenizing, infusing, or any other suitable means.

In some embodiments, where the hydrocarbon-containing material comprises a hydrocarbon-containing fluid, contacting the fluid with the composition may comprise flowing the fluid through the composition. In some embodiments, the composition may be immobilized on a solid support. As one example, the composition may be coated onto an interior surface of a pipe or other fluid conduit and the hydrocarbon-containing fluid may be flowed through the pipe to contact the composition. In some embodiments, the pipe may have a high surface area to increase the contact of the fluid with the composition.

As another example, the composition may be associated with a filtration medium and the fluid may be flowed through the filtration medium. In some embodiments, the composition may be embedded in or bound to the filtration medium. In other embodiments, the composition may only be loosely associated with the filtration medium, for example, as a mechanical mixture. Non-limiting examples of filtration media include biochar, zeolites, sand, diatomaceous earth, and the like. In some embodiments, the filtration medium may be held in a solid support, such as a separation column or a packed bed, for example. The fluid may then be passed through the filtration medium in the solid support at a suitable flow rate to facilitate contact between the fluid and the composition. In other embodiments, the filtration medium and the fluid may be combined in a suitable vessel and, after a suitable period of time, the filtration medium may be separated from the remaining fluid. The filtration medium may be separated from the fluid by precipitation, pressing, screening, centrifugation, or any other suitable separation method.

In some embodiments, the material may briefly be contacted with the composition. For example, a fluid may be flowed through the composition at a relatively high rate. In other embodiments, the material may be contacted with the composition for a desired residency time. For example, the residency time may be at least an hour, a day, or a week. Longer residency times may allow the bacteria in the composition to proliferate and secrete biosurfactants, allowing for greater biosurfactant production and greater contact between the biosurfactants and the hydrocarbon-containing material.

In some embodiments, the material may be contacted with the composition at relatively low temperatures such as below 100° C., below 50° C., below 25° C., or lower.

In some embodiments, the temperature may be the ambient temperature i.e. the temperature in the surrounding environment without the addition of heat. In other embodiments, the temperature may be raised, for example, to lower the viscosity of the hydrocarbon-containing material. The temperature can be raised by electric heating, electromagnetic heating, microwave heating or any other suitable heating means.

In some embodiments, the ratio of the composition to the hydrocarbon-containing material is about 50:1. In some embodiments, the composition comprises between about 1 wt. % and about 50 wt. % of the combined composition and hydrocarbon-containing material mixture. As one example, about 98 wt. % hydrocarbon-containing material may be combined with about 2 wt. % of the composition. In other embodiments, any other suitable ratio may be used.

In some embodiments, the composition is further provided with a catholyte solution, in particular a stabilized or enhanced catholyte solution.

In some embodiments, the hydrocarbon-containing material may be analyzed prior to contacting the material with the composition. For example, the material may be analyzed to determine the hydrocarbon content, water content, solids content, pH, electrical conductivity, or the like. Analysis of the material may be used to determine a suitable dosage of the composition and/or if further processing of the material is desirable. For example, the dosage protocol may be defined by IFT (interfacial tension), shear angle, and kinetic separate laboratory tests.

In some embodiments, the material may be processed prior to contacting the material with the composition. As one example, the water content of the material may be adjusted, for example, by adding water or removing water (e.g. by evaporation). As another example, the material may be concentrated, for example, by centrifugation. As another example, hydrocarbon-containing particulate matter containing relatively large particles may be crushed into a finer form.

Figure 2:
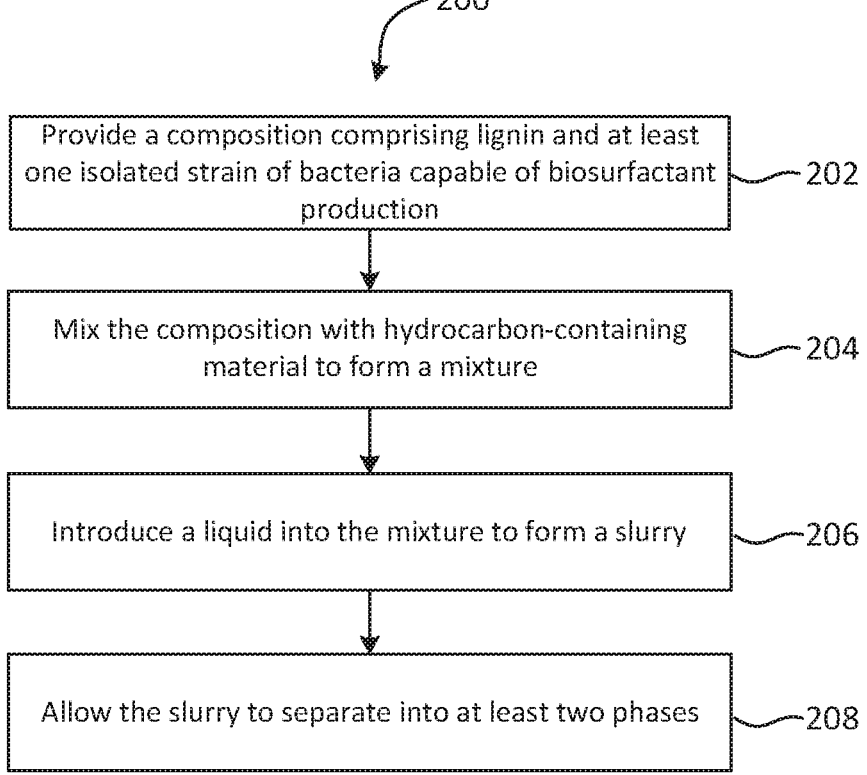
FIG. 2 is a flowchart of another example method for separating hydrocarbons from a hydrocarbon-containing material, according to some embodiments.

FIG. 2 is a flowchart of another example method 200 for separating at least a portion of the hydrocarbons from hydrocarbon-containing material. The method 200 may be used for hydrocarbon-containing particulate matter or a multiphase fluid as described above.

At block 202, a composition is provided comprising lignin and at least one isolated strain of bacteria capable of biosurfactant production. The steps at block 202 may be similar to the steps at block 102 of the method 100 as described above.

At block 204, the composition is mixed with the hydrocarbon-containing material to form a mixture. The composition and the material may be mixed by agitation, aeration, stirring, inversion, blending, homogenizing, or any other suitable method.

In some embodiments, the composition and material are mixed in a mixing device, as described in more detail below. In other embodiments, the composition and material may be mixed manually, for example, by stirring or agitation.

At block 206, a liquid is introduced into the mixture to form a slurry. In some embodiments, the liquid may comprise water. The water may comprise, for example, fresh water, salt water, brine, produced ground water, or any other suitable type of water. In other embodiments, the liquid may comprise another suitable solvent. In some embodiments, the liquid may comprise a catholyte solution as previously described.

In some embodiments, the liquid is added to the mixture. In other embodiments, the mixture is added to the liquid. In some embodiments, the liquid and the mixture may be mixed together, for example, using any of the mixing techniques described above at block 204.

In some embodiments, (where the material comprises little to no native water), between about 25% to about 100% by weight of liquid may be added to the mixture. In some embodiments, about 50% by weight of liquid may be added to the mixture. In other embodiments, any other suitable amount of liquid may be used.

Combining the material with the composition prior to introducing the liquid may avoid diluting the composition in the liquid, thereby maximizing the contact between the material and the lignin and biosurfactant of the composition. However, alternative orders of steps are also possible. For example, in some embodiments, the liquid may be introduced prior to mixing the composition with the material. Alternatively, the liquid may be added to the composition itself and the composition/liquid mixture may be mixed with the hydrocarbon-containing material. Moreover, in embodiments in which the hydrocarbon-containing material already has a relatively high water content, the steps at block 206 may be omitted entirely and no further addition of liquid may be needed.

At block 208, the slurry may be allowed to separate into at least two phases. In some embodiments, the slurry may be allowed to separate under the force of gravity. In some embodiments, the slurry may be separated in a separation vessel, as described in more detail below.

In some embodiments, separation may be facilitated by stirring, agitation, etc. In other embodiments, separation of the slurry may be facilitated by centrifugation. In other embodiments, separation of the slurry may be facilitated by ultrasonic separation techniques.

The two or more phases may comprise, for example, a liquid hydrocarbon (oil) phase, an aqueous phase, and a solid particulate phase. The lignin and bacteria of the composition is expected to move into the aqueous phase. Some hydrocarbon-containing materials may also result in an emulsion phase, gas phase, and the like. In some embodiments, the two or more phases exist as two or more relatively distinct layers. The two or more layers may typically be separated by a boundary, although the layers could also exist without a distinct boundary.

As one example, the two or more layers may comprise an upper layer, a middle layer, and a lower layer. The upper layer may primarily comprise hydrocarbon, the middle layer may primarily comprise water, and the lower layer may primarily comprise particulate matter. This arrangement may be produced when the density of the hydrocarbon is lower than that of water, which is expected for most of the hydrocarbon-containing materials described above. However, if the density of the hydrocarbon is higher than that of water, the upper layer may primarily comprise water and the middle layer may primarily comprise hydrocarbon.

In other embodiments, the two or more phases may be both present without forming layers. For example, droplets of hydrocarbon (oil) may be present in an aqueous phase.

In some embodiments, the method 200 further comprises at least partially removing one or more of the separated phases following the steps at block 208. The term "removing" in this context may refer to isolating, separating, segregating, or sequestering matter from one phase from matter of another phase. For example, at least a portion of the hydrocarbons in the upper layer may be skimmed from top of the separated mixture. As another example, at least a portion of the particulate matter may be withdrawn from the bottom of the separated mixture.

In some embodiments, the separated phases may be removed in two or more stages. For example, one or more of the separated phases may be at least partially removed from the mixture and the remainder of the mixture may undergo a secondary separation step. The secondary separation step may comprise, for example, further gravity separation, decantation, distillation, evaporation, centrifugation, or any other suitable separation technique.

In some embodiments, after at least partially removing one or more of the separated phases, the mixture may be allowed to separate again. In some embodiments, the mixture may first be agitated or stirred to re-combine the separated phases and then allowed to separate again.

In some embodiments, the removed matter may be subjected to further processing, use, and/or disposal. Preferably, the hydrocarbon removed from the mixture may be used as a commercial hydrocarbon product such as bitumen, heavy fuel oil, feedstock for refining, or the like.

In some embodiments, the particulate matter may be disposed (e.g. returned to the environment) or used for other purposes. In some embodiments, the particulate matter may be cleaned prior to disposal or use. The particulate matter may be cleaned by any suitable technique including, for example, water washing and/or microbial degradation.

Similarly, the water may be disposed or used. In some embodiments, the water may be cleaned prior to disposal or use. The water may be cleaned by filtration, microbial degradation, or any other suitable technique. In some embodiments, the water may be re-used as the liquid at block 206 as described above. In other embodiments, the water may be combined with the recovered hydrocarbons to lower their viscosity and/or to transfer the recovered hydrocarbons downstream (e.g. to transfer the recovered hydrocarbons by pipeline to an oil refinery). In some embodiments, at least a portion of the lignin and/or the bacteria of the isolated strain(s) may be recovered from the water for re-use or disposal.

Therefore, the methods 100 and 200 may allow for separation of at least a portion of hydrocarbons from a hydrocarbon-containing material without the use of toxic, and potentially expensive, chemicals. As the lignin/bacteria of the composition automatically move into the aqueous phase, the rheology of the hydrocarbons is not altered by embodiments of the methods described herein. In addition, as the water added at block 206 may be recovered and re-used, the methods 100 and 200 may not require substantial water usage. Moreover, the methods 100 and 200 may be performed without addition of heat; therefore, the energy requirement may be relatively low.

Figure 3:
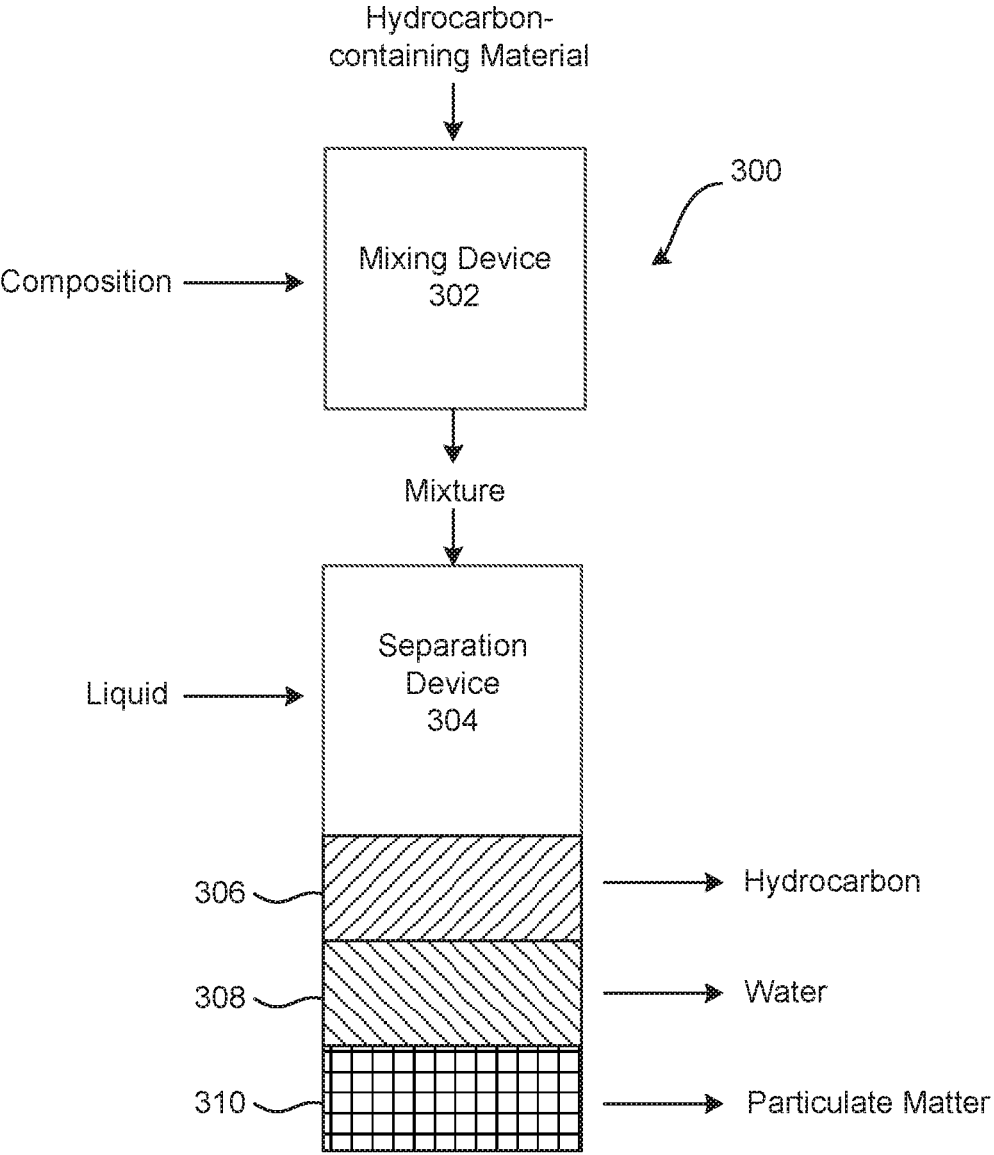
FIG. 3 is a functional block diagram of an example system that may implement the methods of FIGS. 1 and 2.

FIG. 3 shows an example system 300 that may implement one or more embodiments of the methods 100 and 200 described above.

The system 300 may comprise a mixing device 302 and a separation device 304. Non-limiting examples of suitable mixing devices include: a tumbler mixer, an agitator, a drum mixer, a ribbon mixer, a paddle mixer, a homogenizer, or any other suitable mixing device.

A composition comprising lignin and at least one isolated strain of bacteria capable of biosurfactant production, and catholyte solution, where used, and a hydrocarbon-containing material, as described above, may be loaded into the mixing device 302. The composition and material may be mixed therein to produce a mixture.

The separation device 304 may be configured to receive the mixture and a suitable liquid therein and to separate the mixture into two or more phases. In some embodiments, the separation device 304 is a vessel in which the mixture may separate under the force of gravity. In other embodiments, the separation device 304 may be configured to accelerate or facilitate gravity separation. In some embodiments, the separation device 304 may comprise a conventional sand washing plant. In other embodiments, the separation device 304 may be a centrifuge, an ultrasonic separator, or any other suitable type of separation device.

As shown in FIG. 3, in this example, the mixture is separated in the separation device 304 into an upper phase 306, a middle phase 308 and a lower phase 310. For example, the upper phase 306 may comprise hydrocarbons, the middle phase 308 may comprise water or spent catholyte solution or the like, and the lower phase may comprise sand or other particulate matter. In some embodiments, the separation device 304 has one or more outlets (not shown) to allow removal of matter from one or more of the phases 306, 308, 310.

In some embodiments, the system 300 may further comprise a secondary separation device (not shown). The secondary separation device may be configured to receive the matter removed from the separation device 304 and further separate the removed matter into two or more phases. In some embodiments, the secondary separation device may comprise an oil/water separator. The oil/water separator may be configured to receive and at least a portion of the upper phase 306 and/or middle phase 308 to further separate the hydrocarbon and water content of the mixture. In other embodiments, the secondary separation device may comprise a decanter, distillation column, pressure separator, centrifuge, open tank or other separator known in the art for separating mixtures.

In other embodiments, a single device may combine the functions of the mixing device 304 and the separation device 306. In other embodiments, the mixing device 304 may be omitted and the composition and hydrocarbon-containing material may be mixed manually within the separation device 306 or a separate vessel. Other variations are also possible.

EXAMPLES

The invention will now be described in even more detail, by way of example only, with reference to the following non-limiting examples.

Example 1—Phase Separation of Hydrocarbon/Water/Sand Emulsions at Ambient Temperature The performance of an exemplary composition in separating hydrocarbon/water/sand emulsions at ambient temperature was investigated. The emulsions were made using light and heavy oil samples. The ratio of water/oil in the emulsion was the other variable that was tested.

The exemplary composition was labeled as "ActiVata X" and comprised 40-55% liquid sodium lignosulfonate (molecular formula: $C_{20}H_{2}4Na_{2}O_{10}S_{2}$, CAS number: 8061-51-6) and a combination of isolated strains of biosurfactant-producing bacteria.

All the experiments in this Example were conducted at laboratories of Hydrates, Flow Assurance & Phase Equilibria group, Heriot-Watt University.

Experimental Materials and Methods

To conduct the experiments, the following substances were used to prepare the emulsions: sand; a light oil sample, a heavy oil sample, distilled water, and ActiVata X.

The performance of ActiVata X in separation of hydrocarbon from emulsions of oil/water/sand was investigated using static emulsion stability measurement method. The investigations were conducted for emulsions prepared using different oil samples at two water/oil ratios. In order to have a more accurate conclusion, in each case, samples containing ActiVata X (referred to as "experimental sample") were compared against similar samples without this additive (referred to as "reference sample"). Therefore, employing the procedure described below, experimental samples and reference samples were prepared.

Reference sample preparation: To prepare the reference sample, 40 wt. % of the oil, 40 wt. % of water, and 20 wt. % of sand were mixed in a beaker using a dispersion unit (IKA T18 basic-ULTRA TURRAX). The mixing process was continued at 10000 rpm for light oil samples/6000 rpm for heavy oil samples for 5 minutes.

Experimental sample preparation: The experimental samples were made by mixing 39 wt. % of the oil, 39 wt. % of water, 2 wt. % ActiVata X and 20 wt. % of sand. Similar to the reference sample preparation, the mixture was then mixed at 10000 rpm for light oil samples/6000 rpm for heavy oil samples for 5 minutes.

The reference and experimental samples were used to prepare emulsions with varying water content as described below.

Emulsion of light oil (without water): The reference and experimental samples were prepared with light oil as described above. No extra water was added to the samples before final mixing.

Emulsion of light oil+100 wt. % water: The reference and experimental emulsions were prepared with light oil. 100 wt. % water was added prior to the final mixing. Final reference and experimental emulsions were observed to check for any phase changes.

Emulsion of light oil+51.8% water: The reference and experimental samples were prepared with light oil. 51.8% wt. % water was added prior to the final mixing.

Emulsion of heavy oil+100 wt. % water: The reference and experimental emulsions were prepared with heavy oil. 100 wt. % water was added to the samples and then the samples were mixed for 5 minutes at 6000 rpm. Final reference and experimental emulsions were observed over time to check for any phase changes.

Sand sample: To check the amount of sand suspended in the separated oil from the light oil emulsion, a sample was taken from the oil phase in the experimental light oil emulsion with 51.8 wt. % additional water. The oil sample was then washed a few times in a paper filter using pure decane to wash out oil from sand grains. A similar procedure was performed at the same time for a sample taken from the reference light oil emulsion with 51.8 wt. % additional water.

Experimental Results and Discussion

The results of the experiments can be categorized based on the type of oil used for the preparation of the emulsion and the oil/water ratio in the final emulsion.

Figure 4:
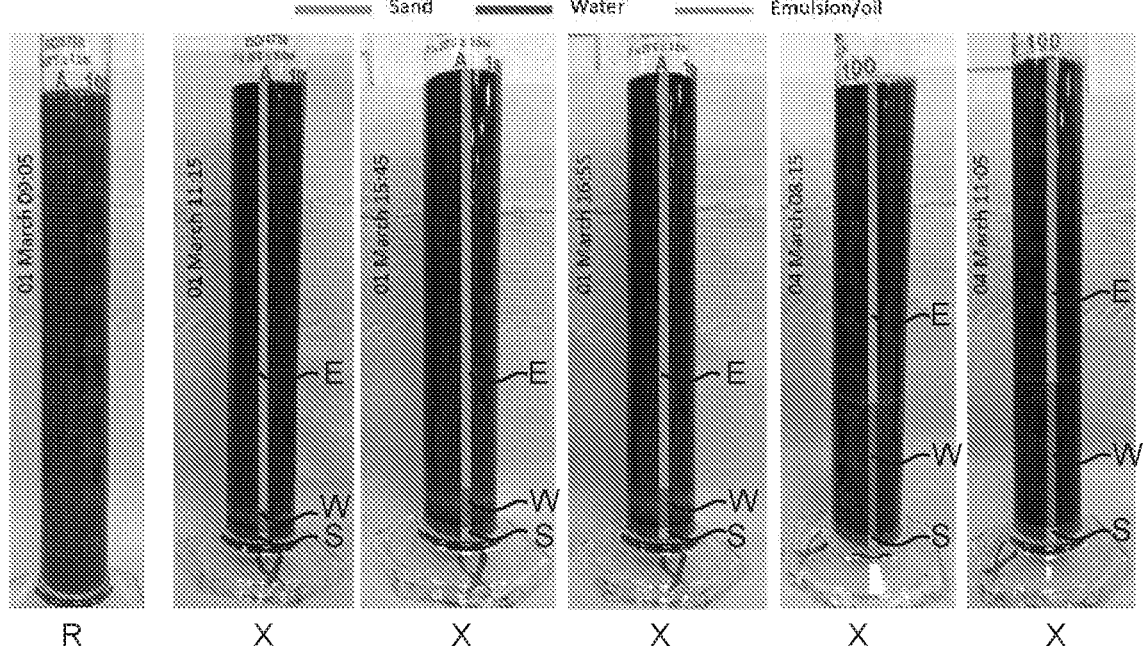
FIG. 4 is a series of photographs showing a reference sample (R) and an experimental sample (X) of a light oil emulsion without extra water at various times after mixing of the emulsion.

Light oil without extra water: Results of these measurements are shown in FIG. 4. Although for the reference sample, phase separation was very slow, for the experimental sample (labeled "X" in FIG. 4), oil phase separation happened much faster. Percentage of water separated at different times for the experimental sample are tabulated in Table 1. The total volume of water separated from the reference sample after 72 hours was less than 3%.

TABLE 1

| Time (minutes) | 100 | 370 | 440 | 4140 | 4410 |
|---|---|---|---|---|---|
| Separated Water (vol %) | 5% | 8% | 9% | 28% | 30% |

Figure 5:
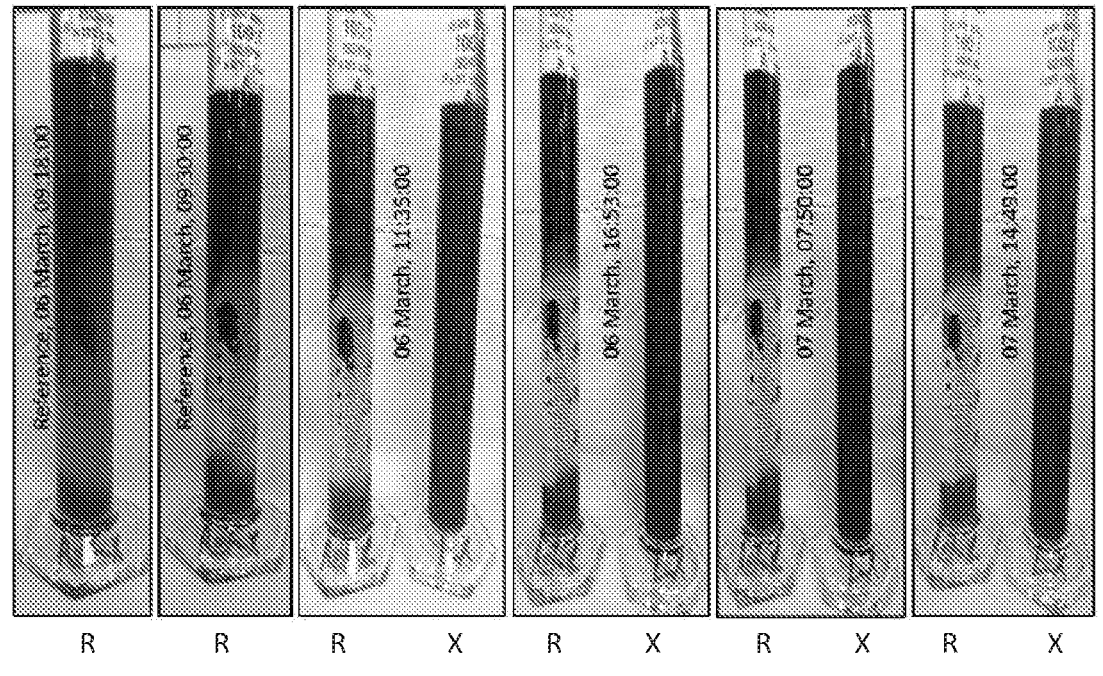
FIG. 5 is a series of photographs showing a reference sample (R) and an experimental sample (X) of a light oil emulsion with 100 wt. % extra water at various times after mixing of the emulsion.

Light oil with 100% water: As can be seen in FIG. 5, in the reference sample, phase separation started very quickly. Over time, water and sands were separated from the emulsion and suspended sand grains were precipitated at the bottom of the graduated cylinder. This allowed the separated water to be more clear and transparent. In comparison to the reference sample, the experimental sample, which contains 2 wt. % of ActiVata X, seemed to be a stable emulsion and even after a few days, no phase separation was observed.

Figure 6:
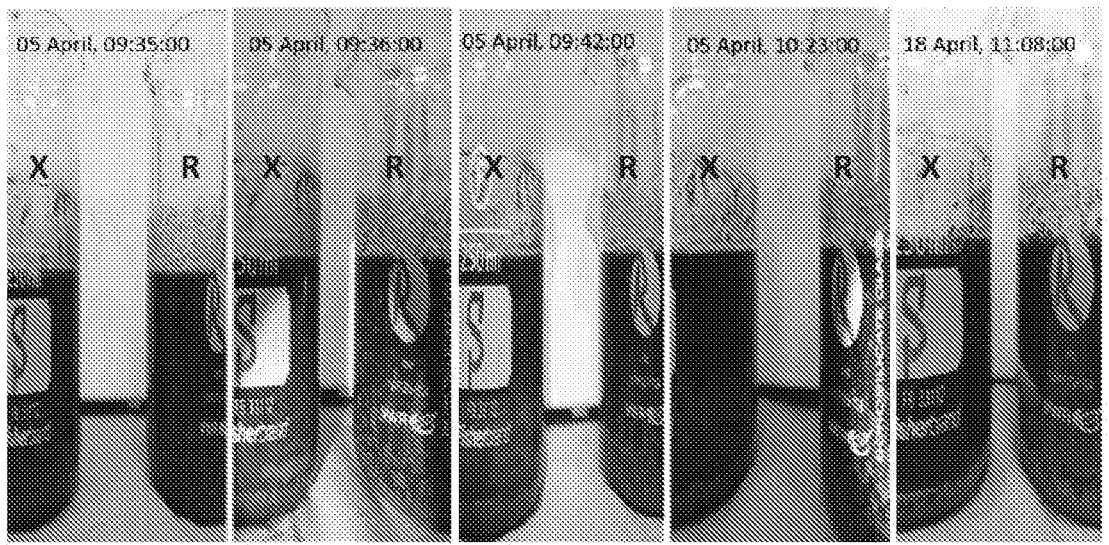
FIG. 6 is a series of photographs showing a reference sample (R) and an experimental sample (X) of a light oil emulsion with 51.8 wt. % extra water at various times after mixing of the emulsion.
Figure 7:
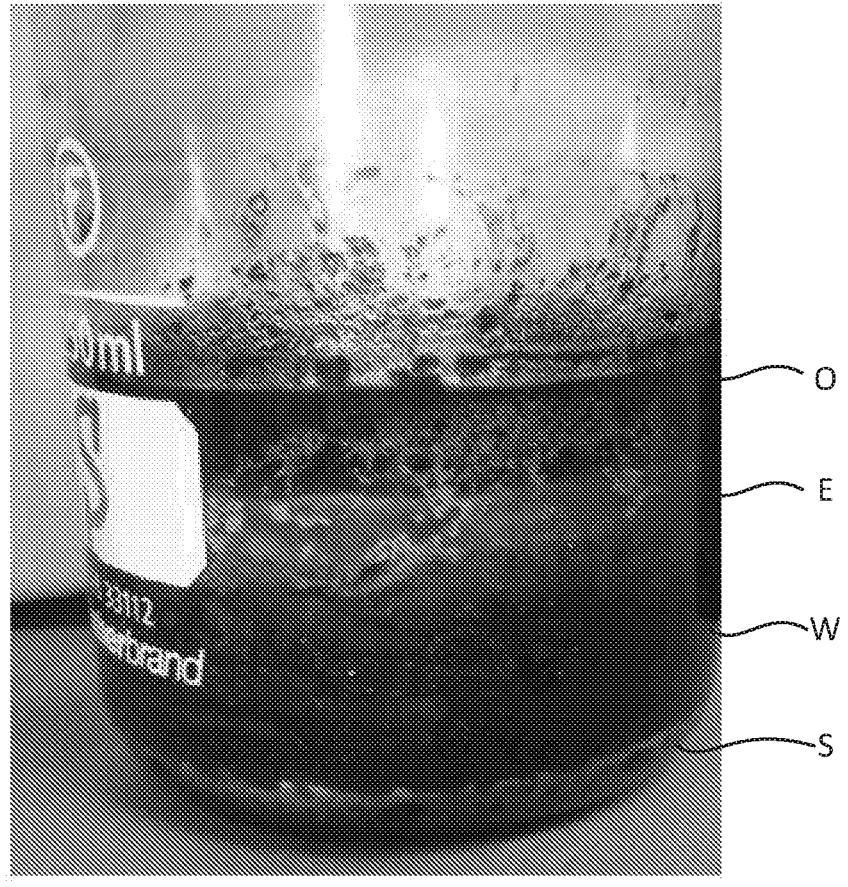
FIG. 7 is a photograph of the experimental sample of FIG. 6 after thirteen days.

Light oil with 51.8 wt. % water: As shown in FIG. 6, for both the experimental and reference sample, phase separation was observed. FIG. 7 shows the experimental sample after 13 days. As shown in FIG. 7, a layer of clean sand (S) grains precipitated at the bottom of the beaker can be observed. From bottom to top, the second layer is a column of separated water (W); however, due to the dark color of the ActiVata X, the water is the same color as ActiVata X. The next layer above the water is emulsion (E) which has a brighter color. As time passed, the thickness of this layer was reduced with separation of water, oil, and sands. Finally a thick layer of oil (O) can be seen on top of the mixture in the beaker. In addition, based on normal visual inspections, the precipitated sands in the beaker containing ActiVata X look to be cleaner than the precipitated sand grains in the reference sample.

Figure 8:
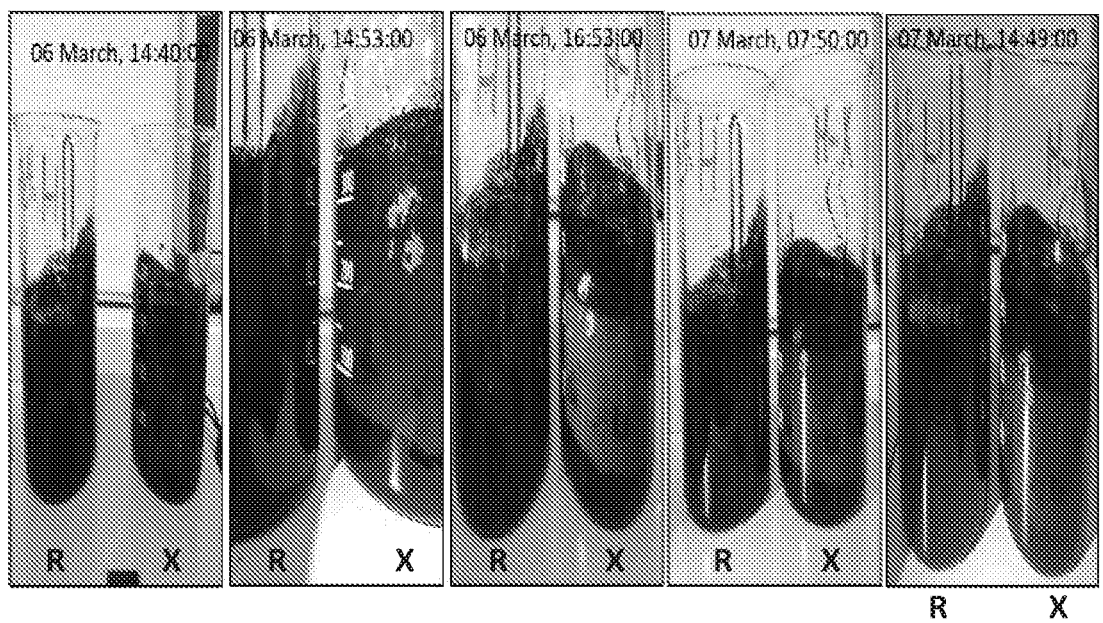
FIG. 8 is a series of photographs showing a reference sample (R) and an experimental sample (X) of a heavy oil emulsion with 100 wt. % extra water at various times after mixing of the emulsion.

Heavy oil with 100% water: As shown in FIG. 8, in a few minutes after preparation of the samples, phase separation happened in the experimental sample containing ActiVata X.

Sand content of the separated oil: Comparison of the weight percentage of the sand in the samples taken from the reference sample and experimental sample of light oil emulsion in the presence of 51.8 wt. % of water, shows a lower sand concentration in the presence of ActiVata X in the emulsion. For the reference sample, the sand wt. % was found to be 6.6%. However, the measured sand content in the sample containing ActiVata X was 5.4%.

Discussion: As described above, for the emulsions prepared using the light oil sample with 100 wt. % additional water, presence of ActiVata X was not effective in improving phase separation. The phase separation in the reference emulsion happened fast; however, in the experimental sample a stable emulsion without any separated phases was observed.

For the light oil emulsion with 51.8 wt. % additional water, phase separation was observed in both the reference and the experimental samples. Therefore, ActiVata X may not be an effective demulsifier for light oil. However, results of the sand content measurements in the oil phase showed that in samples containing ActiVata X, less sand was present in the oil phase.

In contrast to the light oil samples, the presence of the ActiVata X in the emulsion of heavy oil was effective for phase separation in the emulsion. Also, for both the heavy and light samples in the presence of ActiVata X, no detectable changes were observed in the oil.

Various modifications besides those already described are possible without departing from the concepts disclosed herein. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Although particular embodiments have been shown and described, it will be appreciated by those skilled in the art that various changes and modifications might be made without departing from the scope of the disclosure. The terms and expressions used in the preceding specification have been used herein as terms of description and not of limitation, and there is no intention in the use of such terms and expressions of excluding equivalents of the features shown and described or portions thereof.

The invention claimed is:

1. A method for separating hydrocarbons from a hydrocarbon-containing material, the method comprising:
   a) combining the hydrocarbon-containing material, wherein the hydrocarbon-containing material comprises hydrocarbon-containing particulate matter, a hydrocarbon-containing liquid, or a combination thereof, with a composition comprising i) lignin and ii) at least one isolated strain of bacteria capable of producing at least one biosurfactant and/or at least one biosurfactant produced from the at least one isolated strain of bacteria, wherein the composition has a solids content of about 50% or above, to form an admixture;

b) separating out at least a portion of the hydrocarbons from the admixture; and c) recovering at least a portion of the composition from the admixture remaining after step b) for further processing, re-use, or disposal of the composition.

2. The method according to claim 1, further comprising introducing a liquid into the admixture to form a slurry and allowing the slurry to separate into at least two phases under gravity, in a separation tank, and/or facilitated by stirring, agitation, centrifugation, or ultrasonic separation techniques.

3. The method according to claim 1, wherein the hydrocarbon-containing material comprises the hydrocarbon-containing liquid and wherein step a) further comprises flowing the hydrocarbon-containing liquid through the composition.

4. The method according to claim 1, wherein the lignin comprises at least one of lignin nanoparticles and lignin microparticles.

5. The method according to claim 1, wherein the lignin includes lignin particles, at least 20% of the lignin particles being lignin nanoparticles.

6. The method according to claim 1, wherein the composition further comprises a catholyte solution.

7. The method according to claim 2, wherein the liquid is a catholyte solution.

8. The method of claim 1, wherein the portion of the composition recovered in step c) comprises the lignin and/or the at least one isolated strain of bacteria.

\* \* \* \* \*